United States Patent [19]
Preti et al.

[11] 3,986,494
[45] Oct. 19, 1976

[54] METHOD OF PREDICTING AND DETECTING OVULATION

[75] Inventors: George Preti, Philadelphia; George Richardson Huggins, Wallingford, both of Pa.

[73] Assignee: The Trustees of the University of Pennsylvania, Philadelphia, Pa.

[22] Filed: Oct. 30, 1974

[21] Appl. No.: 519,220

[52] U.S. Cl. .............................. 128/2 R; 23/230 B; 23/253 TP; 128/2 W
[51] Int. Cl.² ....................................... A61B 10/00
[58] Field of Search .......................... 128/2 W, 2 R; 23/253 TP, 230 B

[56] References Cited
UNITED STATES PATENTS

| | | | |
|---|---|---|---|
| 3,037,496 | 6/1962 | Melges | 128/2 W |
| 3,406,015 | 10/1968 | Foster | 128/2 W UX |
| 3,406,016 | 10/1968 | Foster et al. | 128/2 W UX |
| 3,472,738 | 10/1969 | Foster | 128/2 W UX |
| 3,842,166 | 10/1974 | Bucalo | 128/2 W X |

OTHER PUBLICATIONS

Michael, R. P. et al., *Science*, 28 May 1971, vol. 172, pp. 964–966.
*J.A.M.A.* vol. 186, No. 5, Nov. 1963, pp. 19 & 20.
Marshall, J. R., *Proceedings of a Research Conf. on Nat. Family Planning*, Jan. 23–26, 1972, pp. 135–143. method"

*Primary Examiner*—Kyle L. Howell
*Attorney, Agent, or Firm*—Paul & Paul

[57] ABSTRACT

A method of monitoring the concentration of a given volatile organic compound commonly found in vaginal secretions is described as providing a reliable diagnostic indication of ovulation, and more particularly is described as providing a simple home-test method of predicting the onset of the fertile period, thereby increasing the reliability of the "rhythm metod" of birth control.

36 Claims, 5 Drawing Figures

METHOD OF PREDICTING AND DETECTING OVULATION

FIELD OF THE INVENTION

The present invention relates to the field of prediction, detection, and diagnosis of ovulation in female mammals through the detection of secondary characteristics occurring before, after or during ovulation, and more particularly to the prediction and detection of ovulation of these secondary characteristics as they appear in human females.

DESCRIPTION OF THE PRIOR ART

There has for many years been a need to predict, detect and diagnose the precise time of ovulation in a given female mammal.

For birth control purposes, the method for predicting the time of ovulation and abstaining from exposure to conception during the "fertile period" surrounding that ovulation is generally referred to as the "rhythm method." The rhythm method has not proven to be a reliable method of birth control, primarily due to the inability of prior art methods to give advance "notice" of the onset of the fertile period. The desirability of improving the reliability of this method need not be discussed at length.

Alternatively, it can be of great importance to determine the precise time of ovulation in order to ensure that fertilization occurs and that offspring are produced. While the prediction of ovulation is of great importance in breeding livestock, particularly thoroughbred race horses or cattle; of even greater importance is the ability to predict whether and when a human female will ovulate so that her chances of producing desired offspring may be increased.

A. DIAGNOSIS OR DETECTION OF OVULATION

In addition to predicting or detecting the occurrence of ovulation, it may be very important to diagnose whether ovulation is indeed occurring. Heretofore, there has been no simple, inexpensive test by which a doctor may diagnose the occurrence of ovulation without awaiting menstruation. Since the occurrence of vaginal bleeding may not be a reliable indicator that ovulation has indeed occurred, and since in many instances it would be desirable to begin treatment for a suspected condition without awaiting the onset of menstruation to determine that ovulation has, in fact, occurred, a need exists for a method to accurately diagnose the occurrence of ovulation at any stage in the menstrual cycle.

The occurrence of ovulation can be established with some certainty through various prior art methods. While the ony irrefutable method of proving ovulation is the occurrence of conception (or occasionally the actual recovery of the egg), several testing techniques are available which may be used to presumptively confirm the occurrence of ovulation. At present, these tests can give a reasonably good indication that ovulation has or is just about to occur, however no simple, inexpensive technique is capable of reliably predicting ovulation more than a day or two in advance.

1. Surgical Techniques

Surgical techniques for detecting ovulation either call for incisions to be made which facilitate the observation of the corpus luteum of the ovary for physical signs of ovulation, or require that attempts be made to recover the ovum from the ovaduct. Neither of these methods have gained widespread acceptance as simple, safe or reliable techniques.

2. Clinical Techniques

Clinical evaluation has often been suggested as a method of detecting the time of ovulation. One such method focuses upon the appearance of pelvic discomfort at the time of expected ovulation. This "mittelschmerz" is thought to be brought about either by distention of the ovary or by peritoneal irritation from bleeding as a result of follicular rupture. Unfortunately, even among those patients who do experience mittelschmerz monthly, the symptom does not appear to be particularly related to the time of ovulation. Similarly, a mucoid vaginal discharge may sometimes be observed which is the result of increasing secretion from the cervix. This discharge may sometimes be noted immediately prior to ovulation and may be observed in conjunction with premenstrual mastalgia, slight edema or tension. While suggesting that ovulation is in fact occurring, the various techniques described above have proved of little value in precisely predicting or detecting the time of ovulation.

Perhaps the most popular and widely used method of detecting and timing ovulation is the use of graphic recording of the waking temperature at basal conditions. Using this method, an extremely dedicated woman with uniform daily habits can determine the time of ovulation within 2 days, after its occurrence. In recording the basal body temperature, a rise in temperature is commonly associated with the beginning of the luteal phase, but can vary from the actual time of ovulation by as much as 72 hours. A theoretical basal body temperature chart is shown in FIG. 1($a$) and actual basal body temperature charts for 4 cycles are shown in FIGS. 2($a$), 3($a$), 4($a$), and 5($a$). Thus, at best, the basal body temperature can indicate the close of the fertile period.

3. Biochemical or Histological Techniques

In more recent years, various biochemical and histological methods have been developed for detection of the precise time of ovulation. These methods include histologic evaluation of endometrial samplings, the use of differential staining techniques on vaginal desquamate and the measurement of hormonal levels throughout the menstrual cycle.

It has long been known that a normal menstrual cycle is accompanied by certain cyclic variations in the concentrations of certain hormones appearing in the blood. Generally, taking the day of ovulation to be day 0 (the point commonly referred to as being "midcycle"), estrogen levels normally begin to rise on approximately day −3, however in some women, may be found to rise as early as day −6, or even earlier. This pre-midcycle estrogen rise is followed by a sharp rise in lutenizing hormone, which is generally accepted to trigger ovulation. Shortly after ovulation, on day +2 or day +3, the level of progesterone begins to rise and remains at sustained levels unitl day +8 or day +10. The theoretical level of estrogens and progesterone are shown in FIG. 1 ($c$) and actual levels for 4 different cycles are shown in FIGS. 2 ($c$), 3($c$), 4($c$), and 5($c$). The theoretical level of lutenizing hormone (LH) is shown in FIG. 1($b$) and the actual LH levels for 4 cycles are shown in FIGS. 2($b$), 3($b$), 4($b$) and 5($b$).

In humans, the preovulatory rise in serum estrogens coupled with a sharp rise in lutenizing hormones (LH) levels as determined by radioimmunoassay and serially drawn blood samples is perhaps the most accurate indicator of impending ovulation. Ovulation most likey occurs 12–24 hours after maximum LH levels. A subsequent rise and persistent high level of serum progesterone indicates that ovulation has occurred. Since these determinations are expensive and not widely available, other clinical parameters are used to predict the fertile period. These rely on various physical and biochemical changes, in the cervical mucous and vaginal mucosa caused by increasing estrogen levels. Each of these individual parameters shows substantial variability but as a composite they yield reliable results.

In recent years, certain other biochemical tests have been developed for the purpose of pinpointing the time of ovulation. One such test, referred to as the cervical mucous test, has been devised for the purpose of predicting the time of ovulation through the measurement of the concentration of glucose present in the cervical mucous. The basis for this test is that during the preovulatory phase, the cervical mucosa and the endometrium secrete glycogen and other polysaccharides to furnish an extrinsic source of energy for the anaerobic metabolism of the sperm and ovum, and of the conceptus during its 6 day journey into the uterine fluids. In order to monitor the concentration of cervical glucose, various tests have been proposed which involve the impregnation of a paper tape with various chemical means which respond to the presence of glucose. Since the concentration level of vaginal glucose differs significantly from that of cervical glucose, it has been necessary to minimize the contact of the impregnated paper tape with glucose found in the vagina itself. This requirement has lead to the development of plastic syringe-like instruments which shield the paper tape from the various vaginal secretions, and particularly vaginal glucose, while the syringe is brought into a position where its tip is in close proximity to tissues which are bathed only in cervical mucous. The syringe is then activated to expose the test tape to the cervical mucous, and contact is maintained for a sufficient length of time (often several minutes) to allow a color indication to take place. The test tape must then again be protected while the syringe-like instrument is removed so that it will not come in contact with undesired glucose in the vaginal secretions. Even if the additional precaution of an aqueous vaginal douche is employed, the possibility of contamination by vaginal secretions remains great, and therefore the reliability of the test is severely hindered. For this reason, the cervical mucous test must be performed by trained personnel (preferably a gynecologist) during an office visit. It then becomes possible to take precautions to ensure that the cervical mucous is properly sampled.

In instances where it is possible to obtain the proper sampling for the cervical mucous test, it has proved reasonably reliable in providing ovulation indicia which are accurate from within one to two days before, to one day after the actual occurrence of ovulation. Therefore, in spite of its clinical drawbacks, the cervical mucous test may prove to be valuable to infertile patients desiring to conceive. It is of little or no use however in avoiding conception, since conception may occur prior to any indication of ovulation.

Another test which has received some attention is the monitoring of salivary alkaline phosphatase levels which generally appear to parallel plasma estradiol (estrogen) levels. Unfortunately, the presence of alkaline phosphatase shows significant daily variations, not only between individuals but also within any given individual. Furthermore, this alkaline phosphatase test tends to provide its characteristic indication during a period ranging from 1 to 10 days prior to the actual occurrence of ovulation. Due to this uncertainty, this test appears to be unreliable in predicting either the onset of the fertile period or the actual occurrence of ovulation.

4. Summary

The following conclusions can be drawn concerning the state of the art in determining the precise time of ovulation in a human female:

1. Although surgical tests may prove to be reliable, they are not practical except on an occasional basis due to their deleterious side effects.
2. Of the chemical tests presently known to the art, the most reliable method of predicting the time of ovulation utilizes the graphing of hormone levels in blood plasma drawn at regular intervals throughout a menstrual cycle. By plotting the levels of lutenizing hormone (LH), estrogens and progesterone in blood plasma, it is possible to establish a good estimate for the time of ovulation.
3. At present, the most widely used technique for detection of ovulation utilizes the recording of basal body temperature. A sustained rise in basal body temperature provides a reasonably good indication that ovulation preceded the beginning of that rise.

B. PREDICTION OF THE FERTILE PERIOD

It is generally accepted that the maximum survival function of spermatozoa capable of fertilizing an ovum is approximately three days following coitus. Although theoretically any coitus prior to ovulation entails a certain risk of pregnancy, as a practical matter, abstinence from sexual intercourse for the three days prior to ovulation is generally considered to be a "safe" period prior to the occurrence of ovulation. It is generally recognized that the ovum is susceptible to fertilization for a matter of hours. In the rabbit or rat, for example, there is a decreased fertility after the sixth hour. It is generally recognized that the human ovum is fertilizable probably for about 12 hours and certainly for no more than 1 day. The human fertile period, then, is made up of no more than 4 days out of the entire menstrual cycle. If it were possible to accurately predict this fertile period, it would theoretically be necessary to either abstain from intercourse or use alternate birth control methods only for that 4 day "fertile period" rather than for the entire menstrual cycle. Heretofore, the only widely used technique for predicting the fertile period of a female has been the method which relies upon basal body temperature determination of ovulation in a plurality of preceding cycles to determine the expected time of ovulation for future cycles. This method is not really directed to ascertaining the precise fertile period for a given cycle, but rather is intended to establish a statistically "dangerous" period during which coitus is likely to produce pregnancy. Since this information is based upon past performance, and since the time of ovulation varies markedly between different individuals as well as between cycles of a given individual, the period for abstinence must be long enough to considerably reduce the possibility of pregnancy.

One method for calculating the period for abstinence which has been suggested is that intercourse be avoided beginning at the time of menses and continuing until a sustained rise in basal body temperature has been observed. Alternatively, a patient may record 12 previous consecutive cycles, noting the longest and shortest cycles experienced during this interval. Since it is generally agreed that menses usually occurs about 14 days after ovulation, it has been suggested that the fertile period in a given cycle is between 18 and 11 days before menstruation. Using this period as the fertile period, the period for abstinence may be calculated by subtracting 18 days from the number of days of the shortest recorded cycle to determine the first unsafe day and by subtracting 11 days from the longest recorded cycle to arrive at the last unsafe day. Since an extremely regular woman would usually have a cycle which varies in length between 26 and 30 days, the shortest period of abstinence would be expected to range from day 8 to day 19, or more than one-third of the total cycle. It has been estimated that only 55% of the naturally occurring menstrual cycles are within the range of 25 to 31 days, and that even the most regular of women may have cycles which vary from 21 to 33 days. Consequently, it may be concluded that the irregularity and extreme length of the required period of abstinence makes the rhythm method based on basal body temperature and statistical prediction unacceptable to all but the most regular and dedicated of women.

Of the various techniques for detecting ovulation which have been considered above, none of these techniques have the practical capability of predicting the onset of ovulation sufficiently in advance to allow the prospective calculation of the period of abstinence. While certain of these tests may occasionally predict ovulation up to 10 days in advance of its occurrence, all of these tests are equally as likely to give no indication of ovulation until affer the onset of the fertile period. This irregularity further precludes any possibility that the tests which do predict ovulation in advance could be used to shorten the period of abstinence since their irregularity would result in periods of abstinence which show no better statistical significance than those based upon the natural occurrence of menstruation. The relative failure of the various techniques discussed above to predict the fertile period in advancee has lead one commentator to conclude:

"The possibility of predicting ovulation by 3–4 days, and thus providing a couple with a period of abstinence no greater than 5 days is intriguing. John Rock, for one, views this approach with some optimism. Should such a method finally be worked out, it would be but another addition, albeit a vital one, to our armamentarium for controlling the population growth of the world. Certainly, in many nations and even among many couples in our own country, much education would be required to convince the male that he should abstain, even for so short an interval as 5 days, and much effort would have to be expended before some males could look upon this as anything but an infringement of their rights as husbands and lovers. It is clear, nevertheless, that if we could find a way to predict ovulation, we would provide a very natural means of family spacing —in fact, the most physiologic means imaginable. Even if it should require somewhat greater effort than the other methods now available, it would be a real boon to many people, regardless of their religious affiliation. It should be kept in mind that even taking a pill once a day requires some effort and intelligence, and certainly the mechanical contrivances now available are, to say the least, inconvenient." . ("The Present Status of Rhythm Techniques", Luigi Mastroianni, Jr., M.D., Clinical Obstetrics and Gynecology, Volume 7, No. 3, 1964, pages 874–875).

SUMMARY OF THE INVENTION

Applicants have found that by monitoring the concentration of any of a number of volatile organic compounds commonly found in vaginal secretions, a reliable diagnostic indication of ovulation may be obtained. Certain of these compounds may also provide such indication in advance of the onset of the fertile period, thereby providing a method for increasing the reliability of the rhythm method of birth control. Unlike prior art methods, the present invention provides a simple, reliable home-test method for predicting, detecting or diagnosing ovulation.

There is a possibility—albeit remote—that odors produced and emitted by humans may play some subtle and as yet unknown role in human reproductive biology. Along with the anecdotal information in the literature, the scientific reports of certain respected researchers have stimulated speculation on this probability. These researchers reported that short chain aliphatic acids ($C_2$–$C_5$) found in the vaginal secretions of estrus female rhesus monkeys acted to induce mating by sexually active male rhesus monkeys. This has been used as the starting point for reports and speculations concerning the role these acid compounds might play in humans. Since some of the speculation has centered upon human vaginal secretions being a probable carrier of human chemical communication, knowledge of the nature and abundance of the small acids as well as other volatiles in this secretion may provide some facts on which to judge the current speculations. Consquently, this theory could explain the regularity with which the abundance of the volatile materials found in these secretions is seen to vary. While primarily under sex steroid control, upon excretion from the body, these compounds may be actively or vestigially targeted at the olfactory organs.

Generally, the method of the present invention comprises the steps of monitoring vaginal secretions for the concentration of at least one volatile organic compound having a molecular weight of between 50 and 350 grams per mole, by providing an indicator means for qualitatively and quantitatively responding to the concentration of said organic compound, whereby the means for indicating that concentration diagnoses the occurrence of ovulation in that menstrual cycle. The volatile organic compound commonly occurring in vaginal secretions of women which are included in this molecular weight range consist of lactic acid, acetic acid, pyridine, 3-hydroxy-2-butanone, propionic acid, iso- and n-butyric acids, phenylacetaldehyde, furfuryl alcohol, isovaleric acid, $\alpha$-methylbutyric acid, dimethylsulfone, n-dodecanol, n-hexadecanol, p-cresol, indole, benzaldehyde, benzoic acid, ethylene gylcol and propylene glycol.

Although the present invention is primarily intended for use by human females, it is also equally applicable to other female mammals, and particularly to domestic cattle and horses. In the breeding of these animals, it is of primary importance to determine the fertile period of a given female animal so that access to a male need be provided for the shortest length of time. This is particularly true of horses where stud service fees are involved and where the prediction of the fertile period of the female animals will allow for the more efficient utilization of each stud animal.

In a first preferred embodiment of the present invention, lactic acid is monitored by an indicator means which responds qualitatively and quantitatively to the concentration of the lactic acid through a color change reaction. In this preferred embodiment, a binder or carrier is impregnated with chemicals which respond with a color change reaction when exposed to lactic acid. In monitoring the concentratioin of lactic acid, a first increase in concentration of lactic acid occurs just prior to the rise in serum estrogens, or approximately 4 days prior to the time of ovulation, thereby indicating the onset of the fertile period of that female. At least 4 days after that increase, a second lactic acid increase indicates the time of ovulation. Twenty-four to 36 hours after this second "ovulatory" increase, coitus will not result in conception. Therefore, the present invention defines a fertile period lasting at least 5 days, during which conception would be possible.

While the lactic acid embodiment of the present invention is primarily intended to predict the onset of the fertile period so that conception may be avioded, once the fertile period is accurately predicted, it is obviously also useful in aiding in producing the conception of offspring.

At the present time, experimental data indicates that the lactic acid embodiment of the present invention would be useful as a birth control method in approximately 80% of the human female population. Since this method utilizes naturally occurring secretions which, if desired, may be tested after being removed from the body, its use entails no adverse physiological side effects. This 80% figure represents a very substantial advance over the old rhythm method and compares favorably to the statistics for other popular methods, many of which are likely to produce undesirable side effects.

In a second preferred embodiment, acetic acid is monitored for the purpose of determining and diagnosing the occurrence of ovulation. A first increase in concentration of acetic acid appears at or just after the time of ovulation, and a second increase occurs during the luteal phase. Applicants have found that the cyclical nature of acetic acid concentrations would be expected to appear in at least 80% of all menstrual cycles. Since concentration maxima do not occur prior to the time of ovulation, this preferred embodiment is particularly useful for diagnosing the time of ovulation, and may be coupled with the lactic acid embodiment discussed above to provide confirmation of the occurrence of ovulation.

The statistical reliability of the present invention may further be improved by determining in advance whether its use is practical for a given woman. This can be accomplished by coupling the use of the indicating means of the present invention with one of the known methods of predicting ovulation, thereby standardizing the use of the present invention for a given female's individual body chemistry.

In the preferred embodiments of the present invention, the indicator means may consist of various compounds which are impregnated in a suitable binder or carrier such as a strip of filter paper, a feminine tampon, or any other chemically inert binder which may be brought into contact with vaginal secretions to produce a desired indication, such as a color change. It is anticipated that these chemically impregnated biners be standardized for color so that a woman may accurately determine the concentration of the volatile organic compound to be detected. In the case of lactic acid detection, for example, this binder would be impregnated with chemicals which produce a bright yellow color when exposed to lactic acid, the intensity of that color varying in accordance with the concentration of lactic acid present. Alternatively, gas chromatographic indicator means may be employed.

Thus, it can be seen that one object of the present invention is to provide a method of reliably diagnosing ovulation in a female mammal. A second object of the present invention is the prediction of the fertile period of a female mammal. A further object of the present invention is the provision of a simple "home-test" method for diagnosing ovulation. Another object of the present invention is the provision of a simple home-test method for predicting the fertile period. One aim of the present invention is the provision of indicator means for qualtatively and quantitatively responding to the concentration of at least one volatile organic compound commonly occurring in the vaginal secretions of female mammals. Another aim of the present invention is to provide a chemically inert binder which is impregnated with chemical means for producing a color change in response to certain given conditions. These and other objects of the present invention will become apparent from the description of the preferred embodiments which appear herein.

DESCRIPTION OF THE PREFERRED EMBODIMENT

Figure 1:
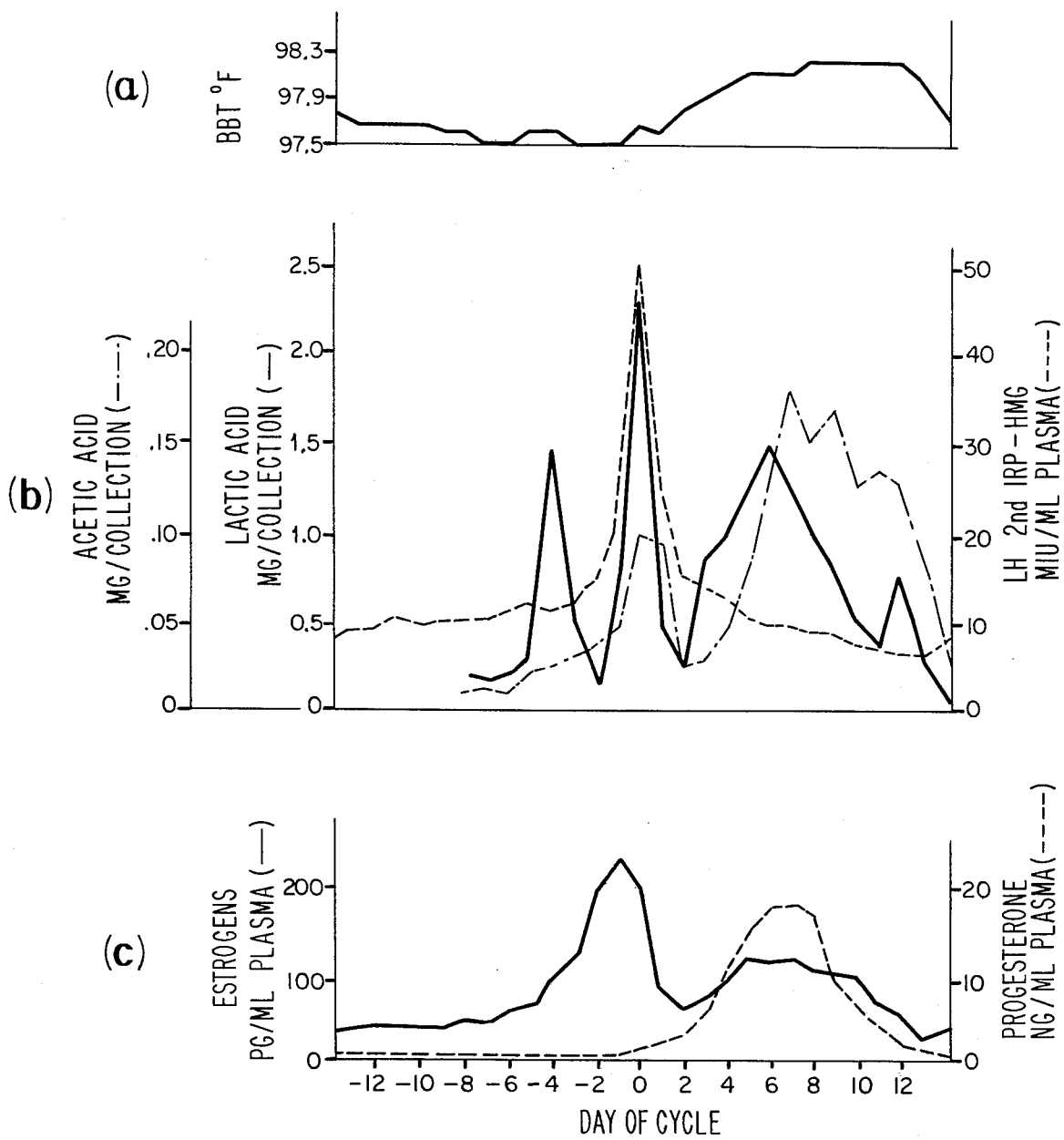
FIG. 1 is a graph showing the theoretical values of basal body temperature, progesterone, lutenizing hormone, estrogens, lactic acid, and acetic acid over the course of one menstrual cycle.

Although specific forms of the invention have been selected for illustration in the drawings, and the following description is drawn in specific terms for the purpose of describing these forms of the invention, this description is not intended to limit the scope of the invention which is defined in the appended claims.

Vaginal secretions are thought to consist of several components; (a) vulval secretions from sebaceous, sweat, Bartholin's and Skeen's glands, (b) mucus secretions from the cervix, (c) endometrial and oviductal fluids, (d) transudate through the vaginal walls, and (e) exfoliated cells of the vaginal mucosa. The type and amounts of (b), (c), and (e) are known to be influenced by biochemical processes which are dependent on sex steroid levels; consequently, metabolic byproducts of these processes should also vary with sex steroid levels. Using gas chromatography (gc) and combination gas chromatagraphy-mass spectrometry (gc-ms), apppplicants have investigated changes in the nature and abundance of volatile chromatographable compounds found in the vagina during the menstrual cycle. Such changes could predict, detect or diagnose changes in circulating hormone levels and thus be diagnostic of ovulation or the fertile period. Predicting either ovulation or this fertile period via these readily accessible metabolites has led to the development of a simplified diagnostic aid for use by the clinician or the individual trying to maximize or minimize the chances of conception.

Applicants found that lactic acid is the major acidic constituent in human vaginal secretions during the time of ovulation and that the amount of it present in the secretion varies with sex steriod levels. Acetic acid is the only small aliphatic acid consistently present in large amounts in most subjects.

Referring to FIG. 1, the theoretical lactic acid curve showing the concentration of lactic acid is plotted over a single menstrual cycle. The variations and concentration of lactic acid can be compared to the variations in basal body temperature, progesterone, estrogen, and acetic acid. FIG. 1 demonstrates that, if the time of ovulation is considered to be day 0, the concentration of lactic acid should theoretically peak first on day $-4$ which is seen to be approximately 1 day before the preovulatory estrogen rise, and is seen to increase a second time at the time of ovulation, or day 0. A third less dramatic increase in lactic acid concentration appears in the postovulatory phase of the cycle. No corresponding increase in lactic acid concentration is expected in the preovulatory phase except that increase which directly precedes the onset of the fertile period.

The information provided for lactic acid concentrations in FIG. 1 is consistent with the experimental data which has resulted from applicant's research. While the preovulatory increase in lactic acid would be expected to occur on day $-4$ in most women, this preovulatory increase appears to consistently precede by approximately 1 day the preovulatory estrogen rise. While this preovulatory estrogen rise normally begins on day $-3$ in some women, it may occur as early as day $-6$ and even, upon occasion, earlier. Thus, strictly speaking, the preovulatory lactic acid increase, which precedes the preovulatory estrogen rise, could occur between day $-4$ and day $-7$, or perhaps even earlier. In no instance known to applicants has the preovulatory lactic acid rise occured later than the preovulatory estrogen rise, thereby indicating that this first lactic acid increase will always occur prior to the fertile period, however in some women its occurrence will precede the onset of the fertile period by more than 1 day.

Figure 5:
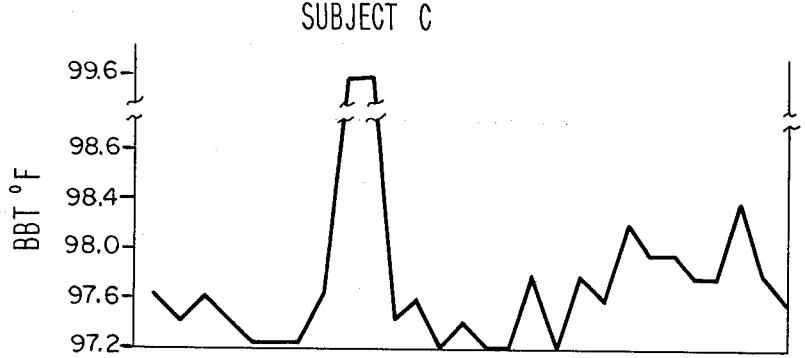
FIG. 5 is a graph of the experimental data for basal body temperature, lutenizing hormone, progesterone, estrogens, and lactic acid as determined for a first cycle of a third subject.
Figure 5:
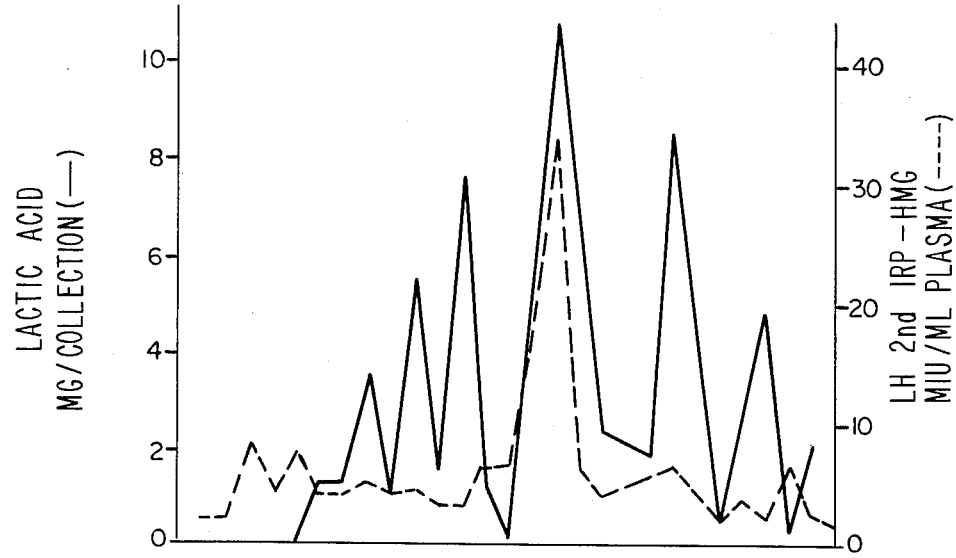
Figure 5:
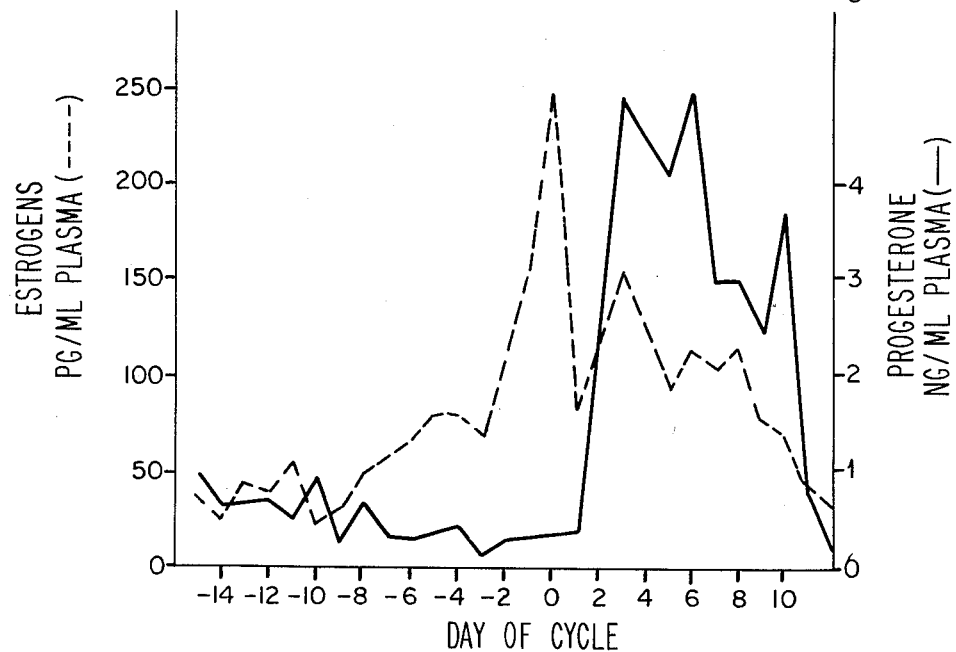

The increase in lactic acid concentration which is observed at the time of ovulation would similarly be expected to vary somewhat from woman to woman. While at no time would it be expected that this midcycle or ovulatory rise in lactic acid would differ from the actual time of ovulation by more than 2 days, it would be expected that the characteristic for this rise would be reasonably uniform within the various menstrual cycles of a given woman. As previously discussed, it would not be expected that the method of the present invention would be applicable to 100% of the women who might wish to employ this method. The cycle of subject C, shown in FIG. 5, is included as an example of an expected type of variation found in a minority of women to whom this method would not generally apply. Therefore, it would be suggested that a given woman could determine the applicability of the method of the present invention to her by utilizing it with one of a number of other known ovulatory indicators, or, alternatively, with the acetic acid preferred embodiment of the present invention, or with one of the other embodiments of the present invention so that a positive correlation of test results could reassure her of the operability and applicability of the present invention to her individual body chemistry.

EXAMPLE 1

Secretions were collected during 22 menstrual cycles from seven healthy, ovulating women. Ovulation was documented in four cycles using radioimmunoassays. In the rest, the day of maximum LH levels (henceforth day 0) was estimated from basal body temperature (BBT) charts. The subjects were asked to record incidents of sexual arousal or coitus and not to use vaginal deodorants or douches. No other restrictions were placed on daily habits or diets.

Pre-cleaned tampons were used for secretion collection. There were inserted before the subject went to sleep and removed the next morning. Beginning 1 or 2 days after the end of menses, samples were collected each night for 10 or 12 consecutive nights, and every other night thereafter until the start of the next menses.

Organic materials were extracted from the tampons by a continuous 24 hour extraction using dichloromethane. Each extract was concentrated to approximately 250 μl via rotary evaporation at room temperature. Chromatography was performed using internal and co-injected standards. Combination gc-ms was carried out at the Monell Chemical Senses Center on selected samples with identifications confirmed by comparison of mass spectra and gc retention times with those from commercially available samples.

In 20 of the 22 cycles studied, lactic acid reached its highest or second highest value within 2 days of the predicted or determined day of ovulation. Eighteen of the 22 cycles showed a second increase in lactic acid concentration which occurred from 3 to 6 days before the midcycle lactic acid peak. Studies of this and other data indicate that this midcycle lactic acid peak closely corresponds to the actual time of ovulation, and it can be seen that in more than 80% of the cycles, the preovulatory increase in lactic acid concentration ocurred immediately prior to the onset of the fertile period.

EXAMPLE 2

In a second series of tests (also conducted at the Monell Chemical Senses Center), blood hormone levels were plotted for four different cycles selected at random from the 22 cycles referred to above. In three of four of these cycles, the pre-midcycle (preovulatory) increase occurred one day before estrogens began to rise. FIGS. 2, 3, 4 and 5 show the four cycles where lactic acid production was plotted with circulating levels of estrogens, progesterone and LH. The pre-midcycle increase occurred one day before estrogens began to rise in 3 of the 4 cycles where blood hormone levels were determined.

FIGS. 2–5 show that the midcycle peak in lactic acid coincides very closely with the midcycle estrogen rise and the LH surge. Maximal amounts of lactic acid varied from subject to subject.

Figure 2:
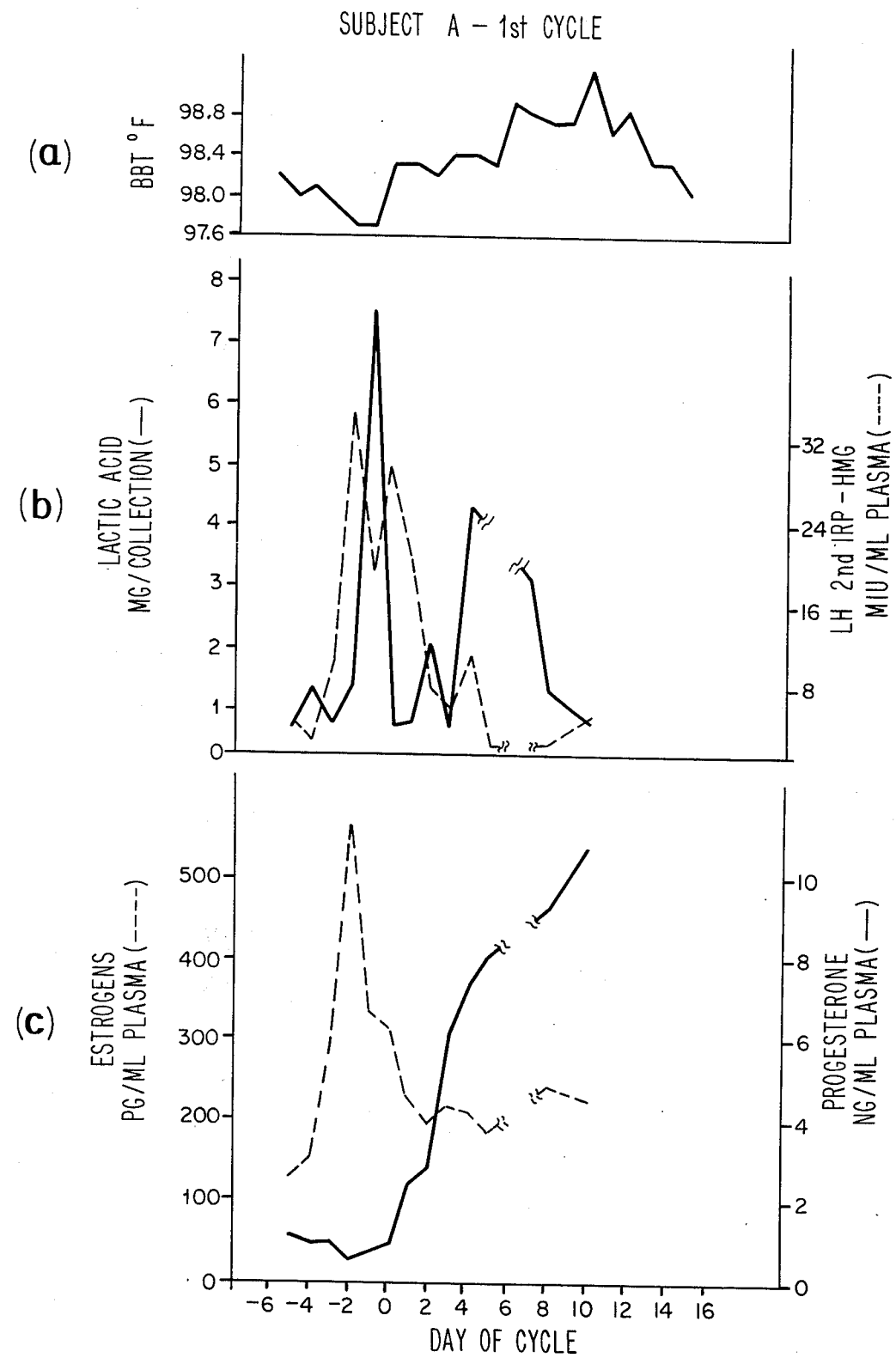
FIG. 2 is a graph of the experimental data for basal body temperaure lutenizing hormone, progesterone, estrogens, and lactic acid as determined for a first cycle of a first subject.
Figure 3:
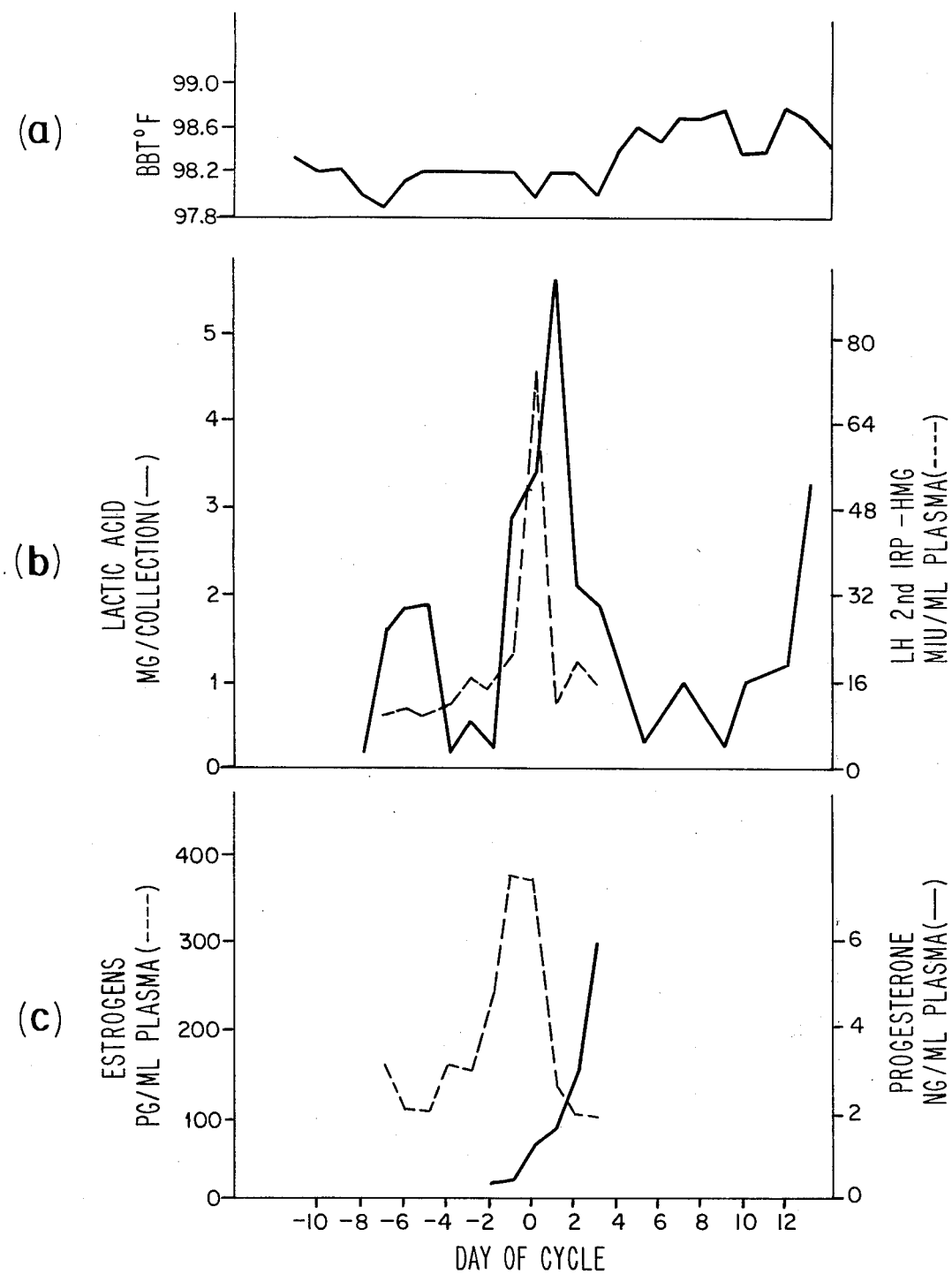
FIG. 3 is a graph of the expermimental data for basal body temperature, lutenizing hormone, progesterone, estrogens, and lactic acid as determined for a second cycle of the first subject.
Figure 4:
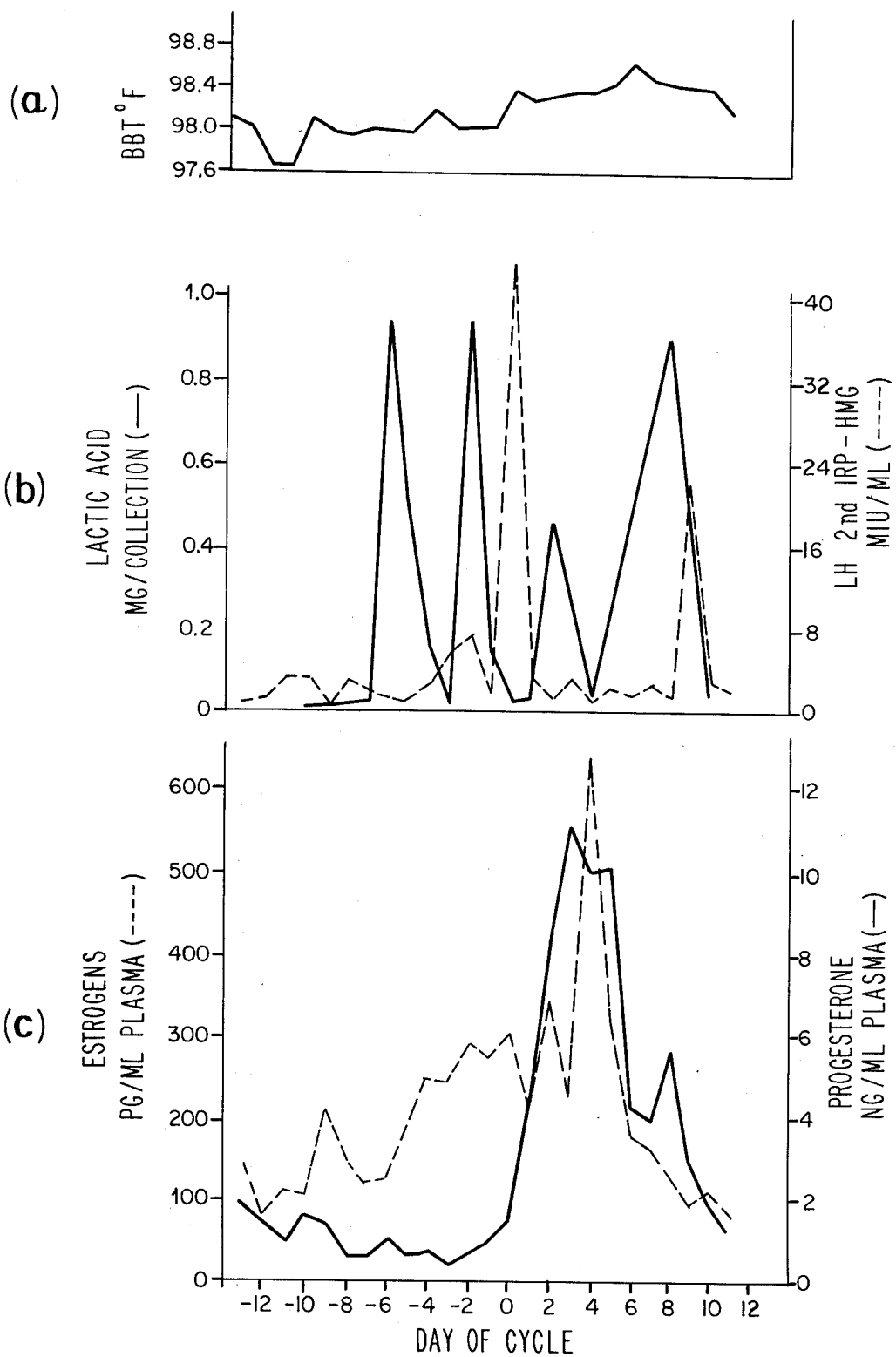
FIG. 4 is a graph of the experimental data for basal body temperature, lutenizing hormone, progesterone, estrogens, and lactic acid as determined for a first cycle of a second subject.

Each of the cycles from subject A seen in FIGS. 2 and 3 show a small rise in lactic acid concentration just before blood estrogens begin to rise. This pre-midcycle rise is much more evident in subject B (FIG. 4). Subject C (FIG. 5) shows three rises and falls in lactic acid concentration during the slow rise in blood estrogens from days −9 through −4. The last and largest of these rises precedes the sharp increase in estrogens on day −3. This subject showed the greatest variability in daily lactic acid throughout each of her 5 cycles.

All cycles in the figures as well as 14 of the remaining 18 cycles show a decrease in lactic acid after midcycle. The second half (luteal phase) of the cycles shows rises in lactic acid which seem to agree with increasing and-/or maximum progesterone levels and the luteal phase estrogen rise. However, late luteal rises in lactic acid seen in 3 of the cycles appear to coincide with the drop in the steroid levels characteristic of this part of the cycle.

The amount of lactic acid collected did not appear to depend upon the amount of secretion collected. In 14 cycles where weights were recorded, maximum amounts of lactic acid coincided with the maximum quantity of secretion in only 2 cycles.

EXAMPLE 3

The acetic acid preferred embodiment also has yielded data indicating that it is a reliable diagnostic test of ovulation.

Referring to FIG. 1, the typical concentration of acetic acid which would be expected to occur over the course of one menstrual cycle is plotted in FIG. 1 (b). A first acetic acid rise is seen to occur at or shortly after the time of ovulation. A second rise is seen to occur between day +6 and day +8. As with the lactic acid graph shown in FIG. 1, the various results for acetic acid may be expected to vary from woman to woman, however the pattern shown in FIG. 1 is consistent with the experimental data produced by applicant's research. Approximately 80% of the cycles tested by applicants showed a cyclical variation of this kind. Once again, a woman would be expected to determine the reliability of an acetic acid test and its applicability to her individual body chemistry by monitoring the concentration of acetic acid and correlating that concentration with other diagnostic ovulatory tests.

Presence of acetic acid was determined in 20 cycles. In 16 of these, the acid varied in a cyclical manner displaying two concentration maxima: one around midcycle, the second, during the luteal phase. Maximum amounts varied from 0.070 mg in subject B to 0.610 mg in subject D. The 4 cycles shown in the figures had maxima which occurred on or after day 0.

Higher acids ($C_3$–$C_5$) were confirmed to be present in only two subjects (D and F). Subject D displayed $C_3$–$C_5$ acids only in the luteal phase of 3 cycles and from day 0 through the luteal phase in a fourth cycle. Subject F showed these acids present almost every day in one cycle with maximal amounts present on day −1. The remaining subjects displayed chromatographic peaks near the correct retention times for n-butyric and isovaleric/α-methlybutyric acids (these two co-eluted); however, mass spectra taken at various times in each subject's cycles showed these peaks contained no detectable amounts of acids.

Thus, it can be seen that the presence of acetic acid may be useful in predicting the time of ovulation, whereas higher acids are not commonly found in the vaginal secretions of most women. At present, there is some indication that when the longer chain acids do occur, they may occur in maximal concentrations at about the time of ovulation.

In addition to the lactic and acetic acid compounds identified above, the following vaginal organic compounds have been unambiguously identified: pyridine, 3-hydroxy-2-butanone, propionic acid, iso- and n-butyric acids, phenylacetaldehyde, furfuryl alcohol, isovaleric acid, α-methylbutyric acid, dimethylsulfone, n-dodecanol, 2-piperidone, n-tetradecanol, and urea (the latter as its bis-trimethylsilyl derivative), n-hexadecanol, p-cresol, squalene, cholesterol, benzaldehyde, benzoic acid, ethylene glycol, and propylene glycol. Tentatively identified from their mass spectra or gc retention times are n-octadecanol and indole. The quantities of each of these substances varied from subject to subject.

Lactic acid has been known to be present in and assumed to be the principal cause of vaginal acidity since the work of Zweifel. This acid is thought to arise, at least in part, by the action of the lactobacillus of Doderlein on vaginal glycogen and/or simpler carbohydrates found in vaginal secretions. Vaginal glucose increases under the influence of estrogen, however, opinions differ as to whether vaginal glycogen actually increases or undergoes a rapid turnover because of estrogen. In either case, estrogens produce increases in carbohydrates available to microflora. However, it is difficult to account for the pre-midcycle and the often seen late luteal rise solely on the basis of increased carbohydrates in the vaginal secretion.

The rapid decreases in lactic acid after midcycle could be due to increased alkaline cervical mucus making its way into the vagina. Semem may also neutralize the vagina and this may account for some of the sharp decreases in lactic acid; however, subject C, who displayed numerous precipitous dips and rises in lactic acid amounts throughout the study denied having intercourse while she was a subject.

Acetic acid present in the vagina may be formed by the same microbial processes which produce lactic acid. The presence of higher acids in only two subjects suggests that conditions conducive to their production in large amounts are not present in all women.

The data presented above was obtained utilizing highly sensitive analytical instrumentation, such as a gas chromatograph, as an indicator means. This type of indicator means has never before been used in a thorough study of human reproductive tract secretions. Use of this instrumentation has offered new approaches in determining hormonal changes via analysis of simple metabolic end products.

In addition to determining the characteristic concentrations of volatile oraganic compounds which are present in vaginal secretions, the present invention also provides for chemical indicator means which respond to the concentration of compounds to be detected, thereby allowing for a reasonably precise prediction of the number of expected days prior to or after the occurrence of ovulation.

In the case of lactic acid, the indicator means may be produced as follows:

A chemically inert binder or carrier, such as a strip of analytical grade filter paper, is successively dipped into the following reagents: (a) 0.5M glucose buffer adjusted to pH 8.8 with sodium hydroxide and containing 0.4 molar semicarbazide (aminourea); (b) 0.027M DPN (diphosophopyridine nucleotide); (c) 3% solution perchloric acid; and (d) a solution containing 2 milligrams of L(+) lactic dehydrogenase per 1 milliliter of distilled water. Upon exposure to as little as 10–20 micrograms of lactic acid, a bright yellw color is observed (within 1 minute), the intensity of that color varying according to the amount of lactic acid present.

An alternative method for producing such a indicator means for lactic acid is to impregnate the chemically inert binder with a solution of 0.4M solution of semicarbazide in a 0.5 molar glucose buffer adjusted to pH 8.8 with sodium hydroxide, and then impregnating that binder with a 0.4 molar solution of ceric sulfate. Upon exposure to lactic acid, a similarly bright yellow color develops with these reagents.

In each of these methods, the observed color and intensity are dependent upon the amount of lactic acid present. Lactic acid concentrations are preferably standardized through exposure of similarly treated impregnated binders to samples containing known amounts of lactic acid. These various intensities are then presented in a chart or other visual manner so that a person utilizing this method can quickly compare the intensity of color which develops upon testing to the intensity given in a standardized color chart. It should be understood that the indicators described above directly respond to the amount of lactic acid to which they are exposed, and therefore, the volume of vaginal secretions to which they are exposed should be reasonably constant. In the case of a feminine tampon or strip of filter paper, the amount of vaginal secretion to be tested would be expected to be reasonably constant. An alternate embodiment of the present invention would contemplate sampling a predetermined amount of vaginal secretion through an alternate technique and exposing that vaginal secretion directly to a reagent solution, gas chromatograph, or other indicator means which would respond qualitatively and quantitatively to the amount of lactic acid present in a given sample, thereby establishing the concentration of that lactic acid. Since there are extremely dramatic variations in the amount of individual volatile organic compounds present throughout the course of a menstrual cycle, any given technique for measuring the amount of that compound present, used at spaced apart intervals throughout the cycle, will correspondingly produce an indication of the concentration of that organic present in the vaginal secretions at the time of sampling. Thus, it can be seen that the specific preferred embodiments discussed above may be adapted to respond qualitatively and quantitatively to the concentration of lactic acid, acetic acid, or other volatile organic compound, depending upon the reagent mixture which is used to impregnate the filter paper, tampon, or other binder.

In utilizing the present invention either to diagnose ovulation or to predict the fertile period, a woman would be provided with a kit having indicator means for qualitatively and quantitatively responding to at least one of the volatile organic compounds commonly found in vaginal secretions. She would then use the indicator means provided for monitoring her vaginal secretions, preferably at spaced apart intervals throughout her menstrual period beginning after the cessation of menses. If the fertile period is to be predicted, these intervals should occur at least every thirty-six hours and preferably every 12 to 24 hours until ovulation has passed. In the case of lacetic acid, a first lactic acid increase would be observed by this method approximately 12 to 24 hours prior to the beginning of the preovulatory estrogen rise, and the woman would be given advance notice that the fertile period would soon begin. If intended as a birth control method, she would then abstain from exposure to conception until after observing a second increase in lactic acid concentration occurring at least four days after the first lactic acid increase. This second increase, which should correspond to, or in some cases follow ovulation, may be confirmed as the ovulatory increase by using other ovulation indicators such as the acetic acid preferred embodiment of the present invention. It would then be recommended to abstain from exposure to conception for an additional 24 to 36 hours to insure that the ovum would no longer be fertilizable. A similar technique would be applicable for the woman desiring to conceive, with the exception that she should maximize her exposure to conception during this fertile period. A similar method would be used for diagnosing the occurrence of ovulation, however, of course, alternative indicator means would be employed for responding qualitatively and quantitatively to any desired volatile organic compound commonly found in the vaginal secretions and having a molecular weight of between 50 and 350 grams per mole. Therefore, it can be seen that the indicator means of the present invention provides a reliable home-test method by which a female may accurately diagnose the occurrence of ovulation, or alternatively predict the onset and termination of her fertile period.

It will be understood that various changes in the details, materials and arrangement of parts which have been herein described and illustrated in order to explain the nature of this invention may be made by those skilled in the art within the principle and scope of the invention as expressed in the following claims.

What is claimed is:

1. A method of diagnosing the onset of the fertile period or ovulation in female mammals comprising the steps of:
   a. monitoring the variation in concentration of the vaginal secretions of one of said mammals for at least one volatile organic compound commonly occurring in the vaginal secretions of said mammals having a molecular weight of between 50 and 350 grams per mole, said variation corresponding to the onset of the fertile period or ovulation of said mammal; and
   b. providing an indicator means for qualitatively and quantitatively responding to the concentration of said volatile organic compound in said vaginal secretions; whereby the response of said means is diagnostic of the onset of the fertile period or ovulation in said female mammal.

2. The invention of claim 1, wherein said female mammal is a human female.

3. The method of claim 2, wherein said organic compound is acetic acid.

4. The method of claim 2, wherein said organic compound is lactic acid.

5. The method of claim 1, wherein said indicator means comprises at least one chemically inert binder impregnated with chemical means for detecting the concentration of said organic compound.

6. The invention of claim 5, wherein the concentration of the volatile organic compound is monitored by bringing each of a plurality of said binders into contact with the vaginal secretions of said female mammal at spaced apart intervals to determine variations in concentration of said organic compound in said secretions.

7. The invention of claim 1, wherein said female mammal is a cow.

8. The invention of claim 1, wherein said female mammal is a mare.

9. A method of diagnosing the onset of the fertile period or ovulation in a given female mammal comprising the steps of:
   a. monitoring the variation in concentration of the vaginal secretions of said mammal for at least one volatile organic compound commonly found in said vaginal secretions having a molecular weight of between 50 and 350 grams per mole; said variation corresponding to the onset of the fertile period or ovulation of said mammal, by
   b. providing indicator means for qualitatively and quantitatively responding to the concentration of said compound in said vaginal secretions; and
   c. evaluating the correspondence of the variation in concentration of said compound to the time of ovulation as indicated by other ovulation indicators; whereby said evaluation is diagnostic of ovulation in said given mammal.

10. The invention of claim 9, wherein said female mammal is a human female.

11. The invention of claim 9, wherein said organic compound is acetic acid.

12. The method of claim 9, wherein said organic compound is lactic acid.

13. The invention of claim 9, wherein said indicator means comprises at least one chemically inert binder impregnated with chemical means for detecting the concentration of said organic compound.

14. The invention of claim 13, wherein the concentration of the volatile organic compound is monitored by bringing each of a plurality of said binders into contact with vaginal secretions of said female mammal at spaced apart intervals to determine variations in concentration of said organic compound in said secretions.

15. The invention of claim 9, wherein said female mammal is a cow.

16. The invention of claim 9, wherein said female mammal is a mare.

17. A method of predicting the fertile period of female mammals comprising the steps of:
   (a). monitoring the variation in concentration of the vaginal secretions of one of said mammals for at least one volatile organic compound having a molecular weight of between 50 and 350 grams per mole commonly found in the vaginal secretions of said mammals by beginning said monitoring at the cessation of menses, said variation corresponding to the onset of the fertile period or ovulation of said mammal; and
   b. providing an indicator means for qualitatively and quantitatively responding to the concentration of said compound in said vaginal secretions; whereby the response of said means predicts the onset of the fertile period or ovulation of said mammal.

18. The invention of claim 17, wherein said female mammals are human females.

19. The invention of claim 18, wherein said organic compound is lactic acid and wherein a first response of said indicator means indicating an increase in said lactic acid concentration is indicative of the onset of the fertile period of said female mammal.

20. The invention of claim 19, wherein a second response of said indicator means indicating an increase in said lactic acid concentration and occurring at least four days after said first response indicates ovulation.

21. The invention of claim 20, wherein said indicator means comprises at least one chemically inert binder impregnated with chemical means for detecting the concentration of said lactic acid.

22. The invention of claim 21, wherein the concentration of lactic acid is monitored by bringing each of a plurality of said binders into contact with the vaginal secretions of said human female at spaced apart intervals to determine the occurrence of said first and second responses.

23. The invention of claim 22, wherein said indicator means also qualitatively and quantitatively responds to the concentration of acetic acid in said vaginal secretions, and wherein a first response indicating an increase in acetic acid and occurring at least four days after said first lactic acid response is indicative of ovulation.

24. A method of predicting the fertile period of a given female mammal comprising the steps of:
   a. monitoring the variation in concentration of the vaginal secretions of said female mammal for at least the lactic acid found in said vaginal secretions, beginning after the cessation of menses, said variation corresponding to onset of the fertile period of said mammal, by
   b. providing indicator means for qualitatively and quantitatively responding to said concentration of lactic acid; and
   c. evaluating the correspondence of said variation in concentration to the fertile period as indicated by other ovulation indicators; whereby said evaluation is diagnostic of ovulation for said given mammal.

25. The invention of claim 24, wherein said female mammal is a human female.

26. The invention of claim 25, wherein said indicator means is a gas-chromatograph.

27. The invention of claim 26, wherein said indicator means is brought into contact with the vaginal secretions of said female mammal at spaced apart intervals to determine variations in concentration of said lactic acid.

28. The invention of claim 27, wherein said indicator means also qualitatively and quantitatively responds to the concentration of acetic acid in said vaginal secretions, and wherein a first response indicating an increase in acetic acid response is indicative of ovulation.

29. The invention of claim 28, wherein said spaced apart intervals occur at least every 36 hours.

30. A method of predicting the fertile period of a human female comprising the steps of:
   a. impregnating a plurality of binders with chemical means for detecting the concentration of lactic acid, thereby forming a plurality of impregnated binders;

b. bringing each of said impregnated binders into contact with the vaginal secretions of said female at spaced apart intervals to determine the variations in concentration of lactic acid present in said secretions; and c. observing the variations in concentration of lactic acid in said secretions as indicated by said impregnated binder, a normal concentration of said lactic acid appearing after the cessation of menses; a first increase in said lactic acid concentration over said normal concentration indicating the onset of said fertile period and a second increase over said normal concentrations occurring at least 4 days after said first increase indicating ovulation.

31. The invention of claim 30, wherein said chemical means for detecting the concentration of lactic acid responds with a color change reaction which varies in intensity proportionally to the concentration of said lactic acid.

32. The invention of claim 31, wherein said means for detecting the concentration of lactic acid comprises a mixture of glucose buffers, sodium hydroxide, semi-carbazide, diphosphopryidene nucleotide, perchloric acid, lactic dehydrogenase and water in the proper concentrations to produce a color change upon exposure to amounts of lactic acid commonly found in the vaginal secretions of human females.

33. The invention of claim 32, wherein each of said binders are impregnated with chemical means for detecting the concentration of lactic acid by the method comprising the steps of:

a. dipping the binder in a solution of 0.5M glucose buffer adjusted to pH 8.8 with sodium hydroxide and containing 0.4M semi-carbazide;

b. dipping the binder into a solution containing 0.027M diphosphopyridene nucleotide;

c. dipping said binder into a 3% solution of perchloric acid; and d. dipping said binder into a solution containing 2 milligrams L (+) lactic dehydrogenase per one ml of distilled water, thereby producing said impregnated binder.

34. The invention of claim 30, wherein said binders comprise analytical grade filter paper impregnated with 0.4M solution of semi-carbazide in a 0.5m glucose buffer adjusted to pH 8.8 with sodium hydroxide, and then with a 0.4M solution of ceric sulfite.

35. A birth control method comprising the steps of:

a. predicting the fertile period of a female mammal by monitoring the variation in concentration of the vaginal secretions of said mammal for lactic acid by beginning said monitoring at the cessation of menses, said variation corresponding to the onset of the fertile period or ovulation of said mammal, b. providing an indicator means for qualitatively and quantitatively responding to the concentration of said compound in said vaginal secretions, wherein a first response of said indicators means showing an increase in said lactic acid concentration is indicative of the onset of the fertile period of said mammal and wherein a second response of said indicator means showing an increase in said lactic acid concentration and occurring at least four days after said first response indicates ovulation, and c. causing said mammal to avoid exposure to fertilization beginning after said first increase and ending at least twenty-four hours after said second increase.

36. A birth control method comprising the steps of:

a. predicting the fertile period of a female mammal by monitoring the variation in concentration of the vaginal secretions of said mammal for lactic acid by beginning said monitoring at the cessation of menses, said variation corresponding to the onset of the fertile period or ovulation of said mammal, b. providing an indicator means for qualitatively and quantitatively responding to the concentration of said compound in said vaginal secretions, wherein a first response of said indicator means showing an increase in said lactic acid concentration is indicative of the onset of the fertile period of said mammal and wherein a second response of said indicator means showing an increase in said lactic acid concentration and occurring at least four days after said first response indicates ovulation, and c. causing said mammal to avoid exposure to fertilization beginning after said first increase and ending at least 36 hours after said second increase.

* * * * *